(12) United States Patent
Chen et al.

(10) Patent No.: US 11,877,887 B2
(45) Date of Patent: Jan. 23, 2024

(54) SENSOR-BASED SHAPE IDENTIFICATION

(71) Applicant: KONINKLIJKE PHILIPS N.V., Eindhoven (NL)

(72) Inventors: Alvin Chen, Cambridge, MA (US); Ramon Quido Erkamp, Swampscott, MA (US); Shyam Bharat, Arlington, MA (US); Kunal Vaidya, Boston, MA (US); Alyssa Torjesen, Charlestown, MA (US); Molly Lara Flexman, Melrose, MA (US); Ameet Kumar Jain, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 358 days.

(21) Appl. No.: 16/970,995

(22) PCT Filed: Feb. 18, 2019

(86) PCT No.: PCT/EP2019/053929
§ 371 (c)(1),
(2) Date: Aug. 19, 2020

(87) PCT Pub. No.: WO2019/162217
PCT Pub. Date: Aug. 29, 2019

(65) Prior Publication Data
US 2020/0397400 A1 Dec. 24, 2020

Related U.S. Application Data

(60) Provisional application No. 62/633,826, filed on Feb. 22, 2018.

(51) Int. Cl.
*A61B 8/08* (2006.01)
*A61B 8/00* (2006.01)
*G01S 15/89* (2006.01)

(52) U.S. Cl.
CPC .............. *A61B 8/0841* (2013.01); *A61B 8/54* (2013.01); *G01S 15/8934* (2013.01)

(58) Field of Classification Search
CPC ......... A61B 8/0841; A61B 8/54; A61B 34/20; A61B 90/90; A61B 5/064;
(Continued)

(56) References Cited

U.S. PATENT DOCUMENTS

| 2003/0060700 A1 | 3/2003 | Solf et al. | |
| 2013/0303878 A1* | 11/2013 | Nevo | A61B 34/20 600/409 |

(Continued)

FOREIGN PATENT DOCUMENTS

| WO | WO-2012056386 A1 * | 5/2012 | ............. A61B 34/20 |
| WO | 2017021172 A1 | 2/2017 | |
| WO | WO-2017021172 A1 * | 2/2017 | ............. A61B 34/20 |

OTHER PUBLICATIONS

PCT/EP2019/053929 ISR & WO, May 31, 2019, 16 Page Document.

*Primary Examiner* — Keith M Raymond
*Assistant Examiner* — Sean A Frith

(57) ABSTRACT

A controller for determining shape of an interventional device includes a memory that stores instructions, and a processor that executes the instructions. When executed by the processor, the instructions cause the controller to execute a process that includes controlling an imaging probe to emit at least one tracking beam to an interventional medical device over a period of time comprising multiple different points of time. The process also includes determining a shape of the interventional medical device, based on a response to the tracking beams received over the period of time from a first sensor that moves along the interventional medical device during the period of time relative to a fixed (Continued)

location on the interventional medical device for the period of time.

17 Claims, 9 Drawing Sheets

(58) Field of Classification Search
CPC .... A61B 2034/2061; A61B 2034/2063; A61B 2090/062; A61B 2090/0811; A61B 2090/364; A61B 2090/374; A61B 2090/376; A61B 2090/378; A61B 2090/3925; A61B 2090/3937; A61B 8/4254; A61B 8/4263; G01S 15/8934; G01S 5/18
See application file for complete search history.

(56) References Cited

U.S. PATENT DOCUMENTS

| | | | | |
|---|---|---|---|---|
| 2014/0357977 | A1* | 12/2014 | Zhou | A61B 34/20 600/409 |
| 2015/0124264 | A1* | 5/2015 | Ramachandran | G01B 11/24 356/601 |
| 2016/0199668 | A1* | 7/2016 | Bharat | A61N 5/1007 600/3 |
| 2016/0228200 | A1* | 8/2016 | Denissen | G01B 11/24 |
| 2016/0249986 | A1 | 9/2016 | Kruger et al. | |
| 2016/0258782 | A1* | 9/2016 | Sadjadi | A61B 34/10 |
| 2017/0348511 | A1* | 12/2017 | Burkholz | A61M 25/0127 |

\* cited by examiner

SENSOR-BASED SHAPE IDENTIFICATION

CROSS-REFERENCE TO PRIOR APPLICATIONS

This application is the U.S. National Phase application under 35 U.S.C. § 371 of International Application No. PCT/EP2019/053929, filed on Feb. 18, 2019, which claims the benefit of U.S. Provisional Patent Application No. 62/633,826, filed on Feb. 22, 2018. These applications are hereby incorporated by reference herein.

BACKGROUND

InSitu technology estimates position of a passive ultrasound sensor in the field of view of a known diagnostic B-mode ultrasound image by analyzing the signal received by the passive ultrasound sensor as the beams of the ultrasound imaging probe sweep the insonified field. Time-of-flight measurements provide the axial/radial distance of the passive ultrasound sensor from the imaging array, while amplitude measurements and knowledge of the beam firing sequence provide the lateral/angular position of the passive ultrasound sensor.

FIG. 1 illustrates a known system for tracking an interventional medical device using a passive ultrasound sensor. In FIG. 1, an ultrasound probe 102 emits an imaging beam 103 that sweeps across a passive ultrasound sensor 104 on a tool tip of an interventional medical device 105. An image of tissue 107 is fed back by the ultrasound probe 102. A location of the passive ultrasound sensor 104 on the tool tip of the interventional medical device 105 is provided as a tip location 108 upon determination by a signal processing algorithm. The tip location 108 is overlaid on the image of tissue 107 as an overlay image 109. The image of tissue 107, the tip location 108, and the overlay image 109 are all displayed on a display 100.

SUMMARY

According to an aspect of the present disclosure, a controller for determining shape and/or path of an interventional device includes a memory that stores instructions, and a processor that executes the instructions. When executed by the processor, the instructions cause the controller to execute a process that includes controlling an imaging probe to emit at least one tracking beam to an interventional medical device over a period of time comprising multiple different points of time. The process also includes determining a shape and/or path of the interventional medical device, based on a response to the tracking beams received over the period of time from a first sensor that moves along the interventional medical device during the period of time relative to a fixed location on the interventional medical device for the period of time.

According to another aspect of the present disclosure, a method for determining shape and/or path of an interventional device includes controlling, by a processor that executes instructions stored in a memory, an imaging probe to emit at least one tracking beam to an interventional medical device over a period of time comprising multiple different points of time. The method also includes determining a shape and/or path of the interventional medical device, based on a response to the tracking beams received over the period of time from a first sensor that moves along the interventional medical device during the period of time relative to a fixed location on the interventional medical device for the period of time.

According to yet another aspect of the present disclosure, a controller for determining shape and/or path of an interventional device includes a memory that stores instructions, and a processor that executes the instructions. When executed by the processor, the instructions cause the controller to execute a process that includes controlling an imaging probe to emit at least one tracking beam to an interventional medical device over a period of time comprising multiple different points of time. The process executed by the controller also includes determining a shape and/or path of the interventional medical device, based on a response to the tracking beams received over the period of time from a first sensor fixed on the interventional medical device during the period of time relative to a fixed location on the interventional medical device during the period of time.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
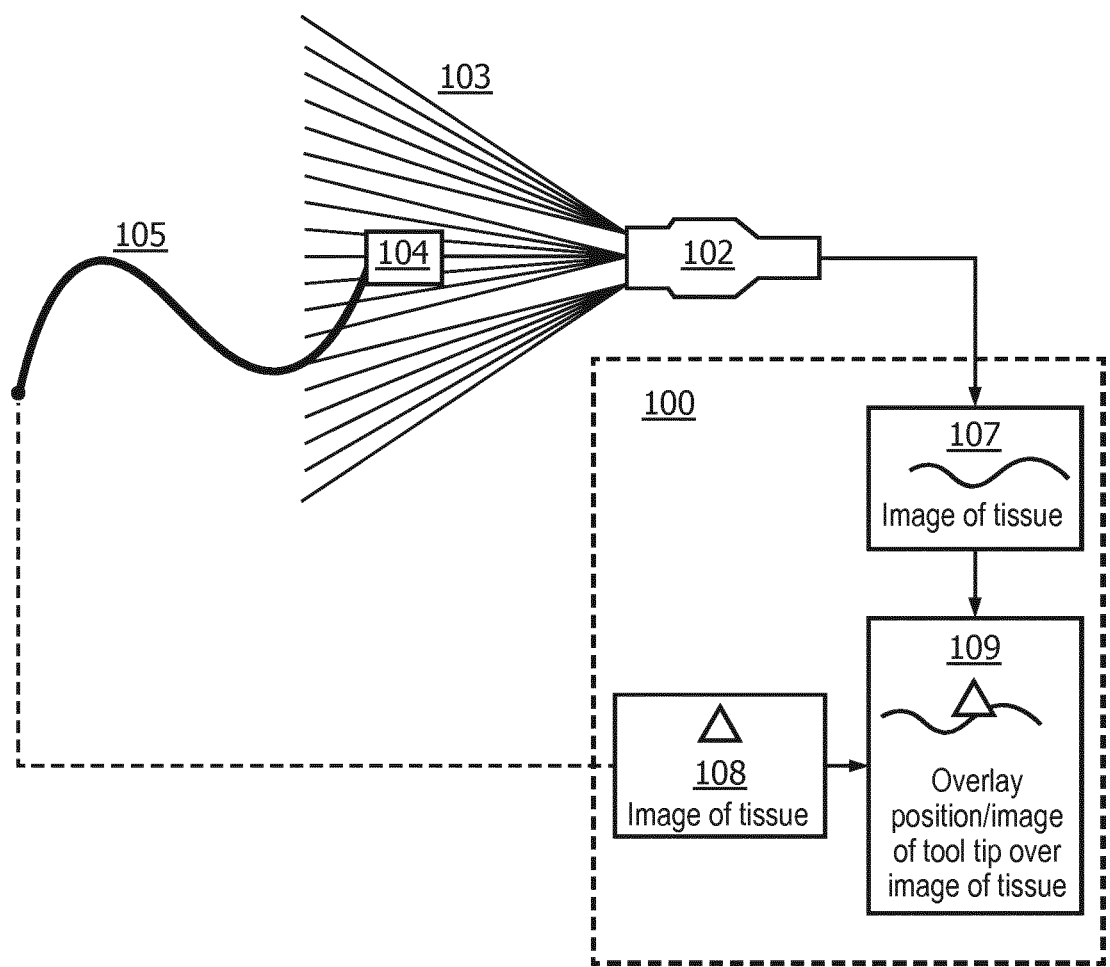
FIG. 1 illustrates a known system for interventional medical device tracking using a passive ultrasound sensor, in accordance with a representative embodiment.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

As described herein, shape of a wire or device can be identified using one or more passive ultrasound sensors such as an InSitu sensor. In embodiments, a first passive ultrasound sensor is movable along a first device relative to a fixed location, and the movable sensor and fixed location are used to identify the shape of the wire or device. In embodiments, a second passive ultrasound sensor at the fixed location serves as a fixed reference marker, for example to compensate for tissue and/or probe motion.

Figure 2A:
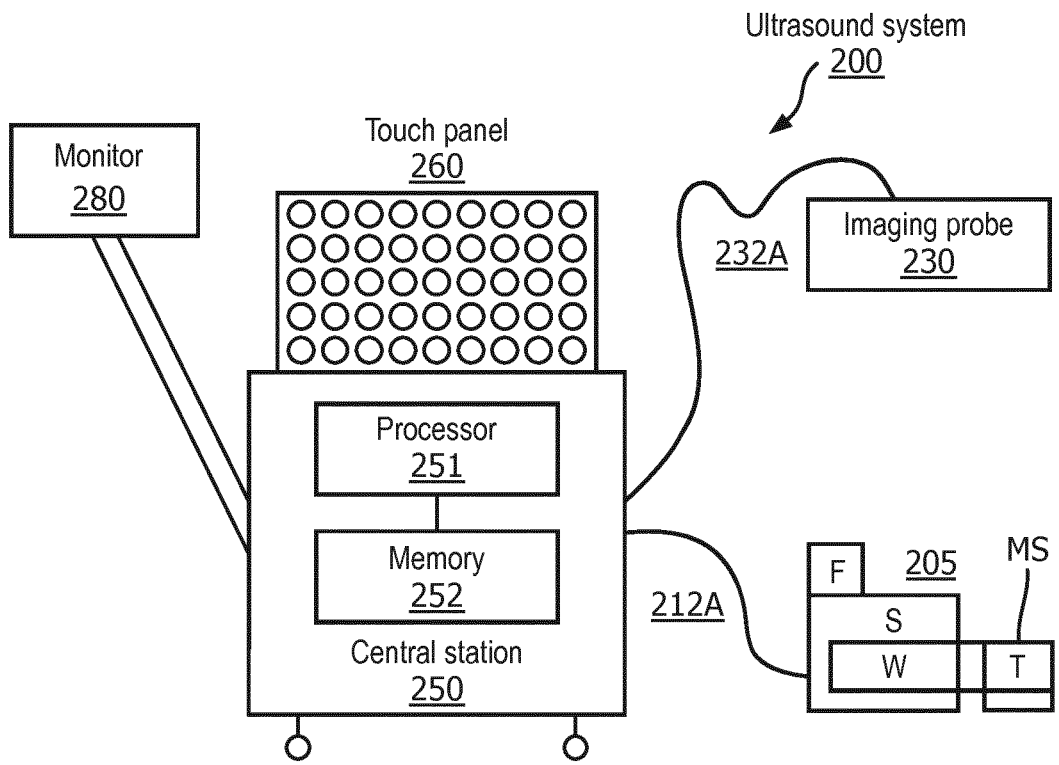
FIG. 2A illustrates an ultrasound system for sensor-based shape identification, in accordance with a representative embodiment.

FIG. 2A illustrates an ultrasound system for sensor-based shape identification, in accordance with a representative embodiment.

In FIG. 2A, an ultrasound system 200 includes a central station 250 with a processor 251 and memory 252, a touch panel 260, a monitor 280, an imaging probe 230 connected to the central station 250 by wire 232A, and an interventional medical device 205 connected to the central station by wire 212A. The interventional medical device 205 in FIG. 2A includes a sheath S and a wire W. A movable sensor MS is movable with a tool T at the end of the wire W of the interventional medical device 205. The sensor MS is movable with tool T at the end of the wire W of the interventional medical device 205, but does not necessarily have to be provided either with a tool T distinguishable from the interventional medical device 205, or at an extremity of any portion of the interventional medical device 205. A fixed location F is disposed on, or as part of, the sheath S of the interventional medical device 205, and may be a visual marker, a fixed sensor, or another form of fixture that can be used to help in determining relative movement of the sensor MS.

Figure 2B:
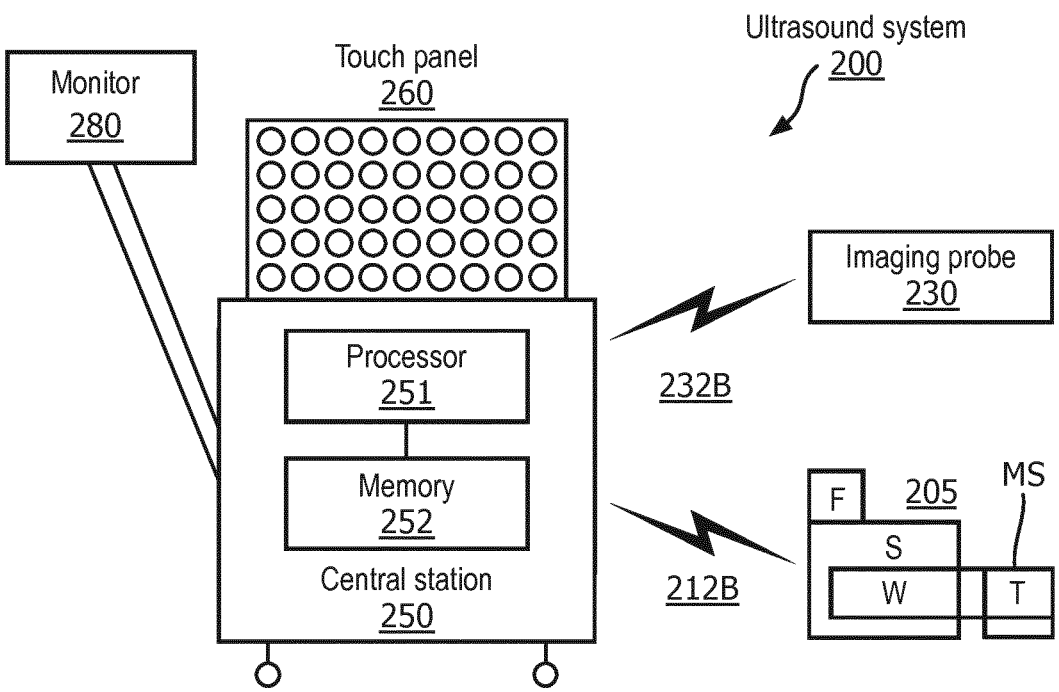
FIG. 2B illustrates another ultrasound system for sensor-based shape identification, in accordance with a representative embodiment.

By way of explanation, an interventional medical device 205 is placed internally into a patient during a medical procedure. Locations of the interventional medical device 205 can be tracked using the movable sensor MS and fixed location F. Moreover, the relationship between the movable sensor MS and fixed location F can be used to determine the shape of the interventional medical device 205. The relationship of the interventional medical device 205, the tool T, the movable sensor MS and the fixed location F may vary greatly from what is shown in FIG. 2A and FIG. 2B. Similarly, the shape of each of the interventional medical device 205, the tool T, the movable sensor MS and the fixed location F may vary greatly from what is shown in FIG. 2A and FIG. 2B.

For example, the movable sensor MS may receive ultrasound tracking beams to help determine a location of the movable sensor MS. Ultrasound tracking beams described herein may be ultrasound imaging beams that are otherwise used to obtain ultrasound images, or may be ultrasound tracking beams that are separate (e.g., separate frequencies, separate transmission timing) from the ultrasound imaging beams. The movable sensor MS may be used passively or actively to respond to the received ultrasound tracking beams. As described herein, ultrasound imaging beams and/or ultrasound tracking beams separate from the ultrasound imaging beams can be used to selectively, typically, or always obtain a location of the movable sensor MS. However, as also noted herein, the tracking can be performed using either or both of the ultrasound imaging beams or completely separate ultrasound tracking beams.

In FIG. 2A, wire 212A and wire 232A are used to connect the interventional medical device 205 and imaging probe 230 to the central station 250. For the imaging probe 230, a wire 232A may not present much of a concern, though the wire 232A may still be a distraction. For the interventional medical device 205, a wire 212A may be used to send back, for example, images when the interventional medical device 205 is used to capture images. However, a wire 212A may be of more concern in that the interventional medical device 205 is at least partly inserted in the patient. Accordingly, replacing the wire 232A and the wire 212A with wireless connections may provide some benefit.

FIG. 2B illustrates another ultrasound system for sensor-based shape identification, in accordance with a representative embodiment.

In FIG. 2B, the wire 232A is replaced with wireless data connection 232B, and the wire 212A is replaced with wireless data connection 212B. Otherwise, the ultrasound system 200 in FIG. 2B includes the same central station 250 as in FIG. 2A, i.e., with the processor 251 and memory 252, touch panel 260, monitor 280, imaging probe 230, and interventional medical device 205. The interventional medical device 205 in FIG. 2B also includes the sheath S and the wire W. The movable sensor MS is movable with the tool T at the end of the wire W of the interventional medical device 205.

In FIG. 2B, the ultrasound system 200 may be an arrangement with an interventional medical device 205 with the movable sensor MS and the fixed location F on board. The interventional medical device 205 may include, e.g., a needle with the movable sensor MS at or near its tip. The movable sensor MS may also be configured to listen to and analyze data from tracking beams, such that the "sending" of the tracking beams from the imaging probe 230, and the "listening" to the tracking beams by the movable sensor MS, are synchronized. Use of tracking beams separate from imaging beams may be provided in an embodiment, but not the primary embodiment(s) of the present disclosure insofar as sensor-based shape identification primarily uses embodiments with only imaging beams.

In FIG. 2A or FIG. 2B, the imaging probe 230 may send a pulse sequence of imaging beams. An explanation of the relationship between the central station 250, imaging probe 230 and the movable sensor MS and fixed location F follows. In this regard, central station 250 in FIGS. 2A and 2B may include a beamformer (not shown) that is synchronized by a clock (not shown) to send properly delayed signals in a transmit mode to elements of an imaging array in the imaging probe 230. In a receive mode, the beamformer may properly delay and sum signals from the individual elements of the imaging array in the imaging probe 230. The ultrasound imaging itself is performed using the imaging probe 230, and may be in accordance with beamforming performed by the beamformer of the central station 250.

The imaging probe 230 may emit imaging beams as tracking beams that impinge on the movable sensor MS (i.e., when the movable sensor MS is in the field of view of the tracking beams). The movable sensor MS may receive and convert the energy of the tracking beams into signals so that the movable sensor MS, or even the interventional medical device 205, can determine the position of the movable sensor MS relative to the imaging array of the imaging probe 230. The relative position of the movable sensor MS can be computed geometrically based on the received tracking beams received by the movable sensor MS, and the relative positions over a period of time can be used to identify the shape of the interventional medical device 205 as it is deployed in a patient.

The fixed location F may be a visual marker fixed, for example, on the sheath at a fixed location. A visual marker may be distinguishable from tissue, such as when the visual marker is made from a material that will reflect and/or absorb energy from the imaging beams in a manner distinguishable from the way that tissue reflects and/or absorbs energy from the imaging beams. In this way, a visual marker can be identified automatically through image processing from the ultrasound images. However, the fixed location F may also be a fixed sensor such as a passive ultrasound sensor. The imaging beams from the imaging probe 230 may impinge on the fixed sensor at the fixed location F when the fixed sensor is in the field of view of the imaging beams as tracking beams. The fixed sensor at the fixed location F may receive and convert the energy of the imaging beams as tracking beams into signals so that the fixed sensor at the fixed location F, or even the interventional medical device 205, can repeatedly determine the position of the fixed sensor at the fixed location F relative to the imaging array of the imaging probe 230. Thus, the imaging probe 230 emits tracking beams to the interventional medical device 205 for a period of time that includes multiple different points of time. For example, tracking beams may be emitted for 30 seconds, 60 seconds, 120 seconds, 180 seconds or any other period of time that include multiple different points of time. Responses to the tracking beams may be collected periodically, such as every second or every $\frac{1}{10}$th second. The responses to the tracking beams may be reflected energy reflected by the movable sensor MS and the fixed sensor at the fixed location F. Alternatively, the responses to the tracking beams may be active signals generated by the movable sensor MS and the fixed sensor at the fixed location F, such as readings of the received energy of the tracking beams.

The fixed location F may also be a visual marker that may be distinguishable from tissue in ultrasound imaging. The fixed location F may also be a marker whose position in space is detectable with respect to anatomy by an alternative modality of imaging, for example X-ray imaging, computed tomography imaging, MRI imaging, optical imaging, or direct visualization. The fixed location F may be a marker whose position in space is detectable with respect to anatomy by an alternative method of sensing such as Doppler ultrasound, electromagnetic tracking, or laser tracking wherein an image is not explicitly generated. Finally, the fixed location F may be a location that is not directly detected by external means, but whose position in space is known at all times with respect to anatomy.

In other embodiments, rather than the fixed location F being tracked by the mechanisms described above (i.e., other than passive ultrasound sensor), the moving sensor MS may be tracked by such means. In these embodiments, the fixed location F may be or include a passive ultrasound sensor tracked by, e.g., Insitu.

Based on the responses to the tracking beams, the processor 251 may determine, for example, absolute position of the movable sensor MS and the fixed sensor at the fixed location F at each of multiple different points in time during the period of time. As a result, movement of the movable sensor MS relative to the fixed sensor at the fixed location F can be determined. The movement reveals the path of the movable sensor MS relative to the fixed location F. And the path reveals the shape of the interventional medical device 205 insofar as the movement of the movable sensor MS relative to the fixed sensor at the fixed location F may correspond to the shape of the interventional medical device 205 is inserted or otherwise moved into the body of the patient. Thus, or instance, when the movable sensor MS is on a needle or a wire as the tool T, the movable sensor MS may move with the needle or wire from a sheath S, such that the movable sensor MS moves relative to the fixed location F on the interventional medical device.

The central station 250 may be considered a control unit or controller that controls the imaging probe 230. As described in FIGS. 2A and 2B, the central station 250 includes a processor 251 connected to a memory 252. The central station 250 may also include a clock (not shown) which provides clock signals to synchronize the imaging probe 230 with the movable sensor MS. Moreover, one or more elements of the central station 250 may individually be considered a control unit or controller. For example, the combination of the processor 251 and the memory 252 may be considered a controller that executes software to perform processes described herein, i.e., to use positions of the movable sensor MS to determine shape of the interventional medical device 205 as the interventional medical device 205 is deployed in a patient.

The imaging probe 230 is adapted to scan a region of interest that includes the interventional medical device 205, the movable sensor MS and the fixed location F. Of course, as is known for ultrasound imaging probes, the imaging probe 230 uses ultrasound imaging beams to provide images on a frame-by-frame basis. The imaging probe 230 can also use separate tracking beams to obtain the location of the movable sensor MS and the fixed location F.

In a one-way relationship, the movable sensor MS and a fixed sensor at the fixed location F may be adapted to convert tracking beams provided by the imaging probe 230 into electrical signals. The movable sensor MS and the fixed sensor at the fixed location F may be configured to provide either the raw data or partially or completely processed data (e.g., calculated sensor locations) to the central station 250, either directly or indirectly (e.g., via a transmitter or repeater located in a proximal end of the interventional medical device 205). These data, depending on their degree of processing, are either used by the central station 250 to determine the location of the movable sensor MS (and the location of the distal end of the interventional medical device 205 to which the movable sensor MS is attached) and the fixed sensor at the fixed location F, or to provide the central station 250 with the location of the movable sensor MS (and the location of the distal end of the interventional medical device 205 to which the movable sensor MS is attached) and the fixed sensor at the fixed location F. The locations from multiple different readings at different times in a period are used to determine shape of the interventional medical device 205, and are accurate insofar as movement of the imaging probe 230 or tissue is accounted for by subtracting or otherwise factoring out the locations of the fixed sensor at the fixed location F.

As described herein, the positions of the movable sensor MS and fixed sensor at the fixed location F are determined by or provided to the central station 250. The positions of the movable sensor MS and the fixed sensor at the fixed location F can be used by the processor 251 to overlay the positions of the movable sensor MS and the fixed sensor at the fixed location F onto an image frame for display on the monitor 280. As a result, movement of the movable sensor, and thus the distal end of the interventional medical device 205, over time relative to the fixed sensor at the fixed location F shows the shape of the interventional medical device 205 as the tool T moves with the end of the wire W. The position of the fixed sensor at the fixed location F can be used to adjust the position of the movable sensor MS, such as to factor out movement of tissue that affects the locations of the movable sensor MS in an absolute coordinate system. In other words, a movable sensor MS may move relative to a fixed location F based on movement of tissue that contacts the movable sensor MS, in addition to operational movement of the movable sensor MS with the tool T at the end of the wire W. In another representative embodiment, instructions stored in memory 252 are executed by the processor 251 to determine positions of the movable sensor MS and the fixed sensor at the fixed location F relative to an image frame, and to overlay the positions of the movable sensor MS and the fixed sensor at the fixed location F. Accordingly, the shape of the interventional medical device 205 is derived from the changing locations of the movable sensor MS relative to the fixed sensor at the fixed location F, as the tool T moves with the end of the wire W. Again, the locations of the fixed sensor at the fixed location F can be factored out to account for movement of tissue or even movement of the imaging probe 230 that affects the perceived location of the movable sensor MS in an absolute coordinate system.

Broadly, in operation, the processor 251 initiates a scan by the imaging probe 230. The scan can include emitting imaging beams as tracking beams across a region of interest. The imaging beams are used to form an image of a frame; and as tracking beams to determine the location of the movable sensor MS and the fixed sensor at the fixed location F. The locations in turn are used to determine shape as the movable sensor MS moves relative to the fixed location F over a period of time. As can be appreciated, the image from imaging beams is formed from a two-way transmission sequence, with images of the region of interest being formed by the transmission and reflection of sub-beams. Additionally, in a one-way relationship, the imaging beams as tracking beams incident on the movable sensor MS and the fixed sensor at the fixed location F and may be converted into electrical signals (i.e., rather than or in addition to reflecting the tracking beams). In a two-way relationship, the imaging beams as tracking beams are reflected by the movable sensor MS and the fixed sensor at the fixed location F, so that the imaging probe 230 determines the location of the movable sensor MS and the fixed sensor at the fixed location F using the reflected tracking beams.

As noted above, data used to determine locations of the movable sensor MS and the fixed sensor at the fixed location F may comprise raw data, partially processed data, or fully processed data, depending on where location is to be determined. Depending on the degree of processing, these data can be provided to the processor 251 for executing instructions stored in the memory 252 (i.e., of the central station 250) to determine the positions of the movable sensor MS and the fixed sensor at the fixed location F in the coordinate system of ultrasound images from the beamformer. Alternatively, these data may include the determined positions of the movable sensor MS and the fixed sensor at the fixed location F in the coordinate system which is used by the processor 251 when executing instructions stored in the memory 252 to overlay the positions of the movable sensor MS and the fixed sensor at the fixed location F on the ultrasound image in the monitor 280. To this end, the beamformer of the central station 250 may process the beamformed signal for display as an image of a frame. The output from the beamformer can be provided to the processor 251. The data from the movable sensor MS and the fixed sensor at the fixed location F may be raw data, in which case the processor 251 executes instructions in the memory 252 to determine the positions of the movable sensor MS and the fixed sensor at the fixed location F in the coordinate system of the image; or the data from the movable sensor MS and the fixed sensor at the fixed location F may be processed by the interventional medical device 205 to determine the locations of the movable sensor MS and the fixed sensor at the fixed location F in the coordinate system of the image. Either way, the processor 251 is configured to overlay the positions of the movable sensor MS and the fixed sensor at the fixed location F on the image on the monitor 280. For example, a composite image from the imaging beams as tracking beams may include the image of tissue and actual or superposed positions of the movable sensor MS and the fixed sensor at the fixed location F, thereby providing real-time feedback to a clinician of the position and history of the movable sensor MS (and the distal end of the interventional medical device 205) and the fixed sensor at the fixed location F, each relative to the region of interest and to each other. As can be appreciated, superposing of the positions of the movable sensor MS in context with historical positions and in context of the fixed sensor at the fixed location F, enables complete real-time in-situ visualization of shape of the interventional medical device 205 as the movable sensor MS projects from the interventional medical device with, e.g., the wire W or tool T.

Figure 2C:
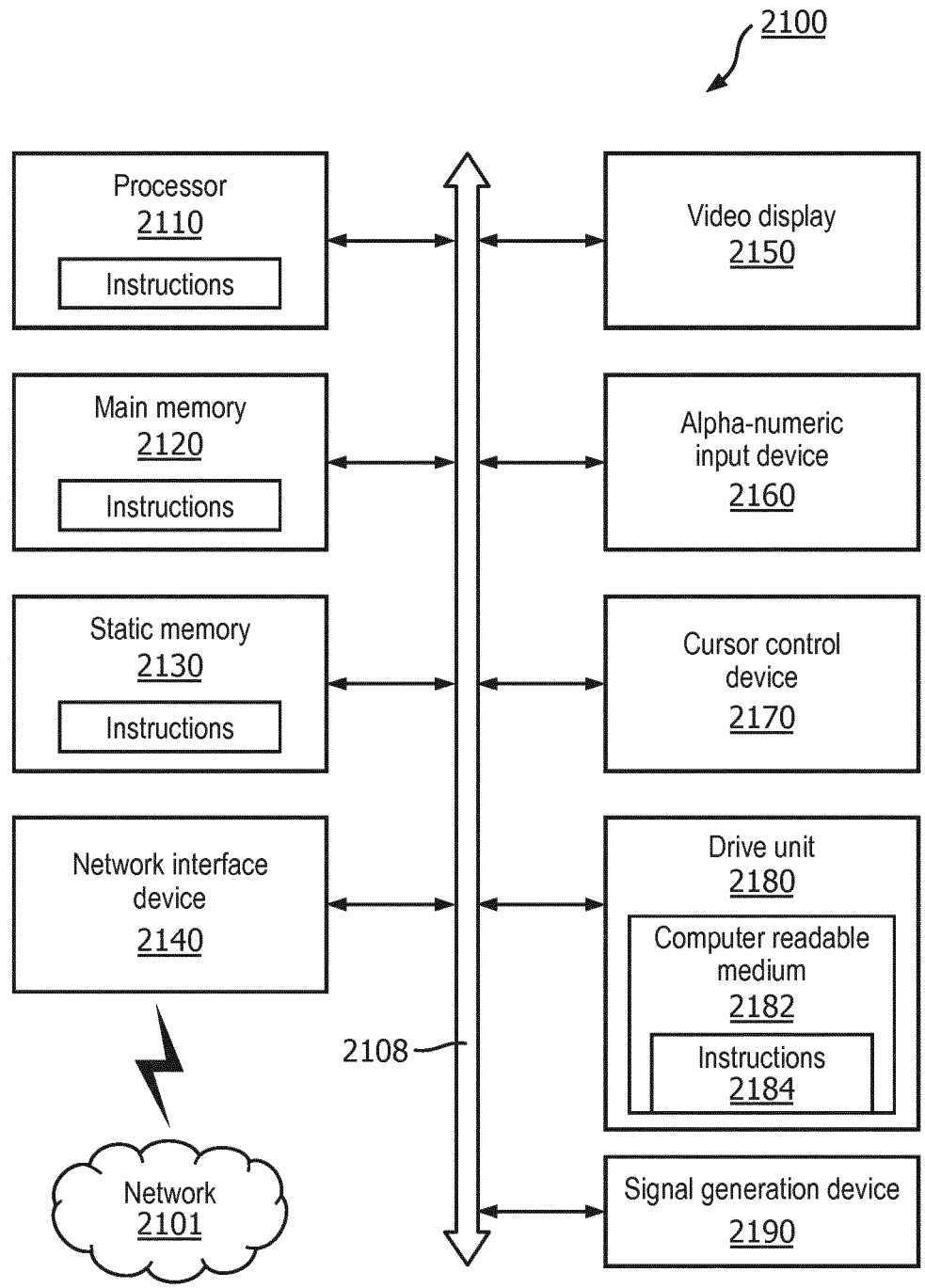
FIG. 2C is an illustrative embodiment of a general computer system, on which a method of sensor-based shape identification can be implemented, in accordance with a representative embodiment.

FIG. 2C is an illustrative embodiment of a general computer system, on which a method of sensor-based shape identification can be implemented, in accordance with a representative embodiment.

The computer system 2100 can include a set of instructions that can be executed to cause the computer system 2100 to perform any one or more of the methods or computer based functions disclosed herein. The computer system 2100 may operate as a standalone device or may be connected, for example, using a network 2101, to other computer systems or peripheral devices. Any or all of the elements and characteristics of the computer system 2100 in FIG. 1C may be representative of elements and characteristics of the central station 250, the imaging probe 230, or even the movable sensor MS and the fixed sensor at the fixed location F in FIGS. 2A and 2B.

In a networked deployment, the computer system 2100 may operate in the capacity of a client in a server-client user network environment. The computer system 2100 can also be fully or partially implemented as or incorporated into various devices, such as a control station, imaging probe, passive ultrasound sensor, stationary computer, a mobile computer, a personal computer (PC), or any other machine capable of executing a set of instructions (sequential or otherwise) that specify actions to be taken by that machine. The computer system 2100 can be incorporated as or in a device that in turn is in an integrated system that includes additional devices. In an embodiment, the computer system 2100 can be implemented using electronic devices that provide video or data communication. Further, while the computer system 2100 is illustrated, the term "system" shall also be taken to include any collection of systems or sub-systems that individually or jointly execute a set, or multiple sets, of instructions to perform one or more computer functions.

As illustrated in FIG. 1C, the computer system 2100 includes a processor 2110. A processor 2110 for a computer system 2100 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. Any processor described herein is an article of manufacture and/or a machine component. A processor for a computer system 2100 is configured to execute software instructions to perform functions as described in the various embodiments herein. A processor for a computer system 2100 may be a general-purpose processor or may be part of an application specific integrated circuit (ASIC). A processor for a computer system 2100 may also be a microprocessor, a microcomputer, a processor chip, a controller, a microcontroller, a digital signal processor (DSP), a state machine, or a programmable logic device. A processor for a computer system 2100 may also be a logical circuit, including a programmable gate array (PGA) such as a field programmable gate array (FPGA), or another type of circuit that includes discrete gate and/or transistor logic. A processor for a computer system 2100 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 2100 includes a main memory 2120 and a static memory 2130 that can communicate with each other via a bus 2108. Memories described herein are tangible storage mediums that can store data and executable instructions, and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 2100 may further include a video display unit 2150, such as a liquid crystal display (LCD), an organic light emitting diode (OLED), a flat panel display, a solid-state display, or a cathode ray tube (CRT). Additionally, the computer system 2100 may include an input device 2160, such as a keyboard/virtual keyboard or touch-sensitive input screen or speech input with speech recognition, and a cursor control device 2170, such as a mouse or touch-sensitive input screen or pad. The computer system 2100 can also include a disk drive unit 2180, a signal generation device 2190, such as a speaker or remote control, and a network interface device 2140.

In an embodiment, as depicted in FIG. 1C, the disk drive unit 2180 may include a computer-readable medium 2182 in which one or more sets of instructions 2184, e.g. software, can be embedded. Sets of instructions 2184 can be read from the computer-readable medium 2182. Further, the instructions 2184, when executed by a processor, can be used to perform one or more of the methods and processes as described herein. In an embodiment, the instructions 2184 may reside completely, or at least partially, within the main memory 2120, the static memory 2130, and/or within the processor 2110 during execution by the computer system 2100.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 2182 that includes instructions 2184 or receives and executes instructions 2184 responsive to a propagated signal; so that a device connected to a network 2101 can communicate video or data over the network 2101. Further, the instructions 2184 may be transmitted or received over the network 2101 via the network interface device 2140.

Figure 3:
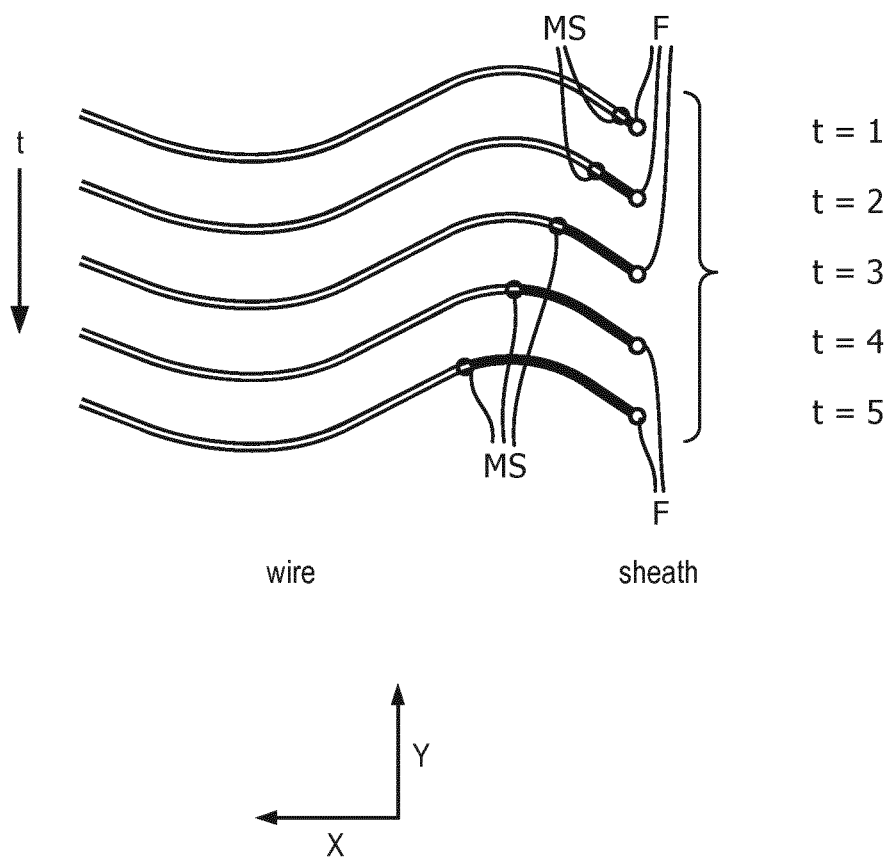
FIG. 3 illustrates an interventional medical device used for sensor-based shape identification, in accordance with a representative embodiment.

FIG. 3 illustrates an interventional medical device used for sensor-based shape identification, in accordance with a representative embodiment.

Sensor-based shape identification can be used to quantify a shape using passive ultrasound sensors as shown in FIG. 3. A movable sensor MS is a first sensor that is movable along a first device to obtain the shape of the first device. The movable sensor MS moves as a wire W is drawn from a sheath S. A fixed sensor at a fixed location F is a second sensor located on a second device and remains static with respect to anatomy. The fixed sensor at the fixed location F remains stationary in both the horizontal (X) plane and the vertical (Y) plane as the wire W is drawn from the sheath S. In three-dimensional ultrasound, the fixed sensor remains stationary in the horizontal (X) plane, the vertical (Y) plane, and the depth (Z) plane, and the movable sensor is tracked in all three of these planes to obtain the three-dimensional shape. The fixed sensor at the fixed location F serves as a fixed reference marker, e.g. to compensate for tissue or probe motion. In other words, the movable sensor MS is a first sensor that moves relative to a second sensor fixed at a fixed location F for a period of time. In FIG. 3, the movable sensor MS is shown to move at five different positions at different times, i.e., t=1, t=2, t=3, t=4, and t=5 in a period. A pullback or other related motion of the movable sensor MS as the first sensor relative to the fixed sensor fixed at the fixed location F is tracked, and the tracking position history is integrated to obtain shape. The locations can be tracked using methodology such as the InSitu methodology which tracks passive ultrasound sensors with either imaging beams alone, or with imaging beams and completely separate tracking beams such as interleaved separate imaging beams and tracking beams.

The fixed location F may also be a visual marker or a marker that is detectable by an alternative modality of imaging or sensing, including but not limited to X-ray imaging, computed tomography imaging, MRI imaging, optical imaging, Doppler ultrasound, electromagnetic tracking, laser tracking or direct visualization, or a marker whose position in space is known at all times with respect to anatomy without explicit sensing.

In FIG. 3, the device containing the movable sensor MS as the first sensor is a wire, and the device containing the fixed sensor fixed at the fixed location F as the second sensor is a conduit or sheath. However, the reverse mechanism is also possible. The fixed sensor as the second sensor may also be referred to as a reference sensor.

Specifically, in FIG. 3, the first device containing the movable sensor MS is a wire, and the second device containing the fixed sensor (i.e., the reference sensor) is a conduit or sheath. The movable sensor as the first sensor is tracked as the wire is moved along the inner channel of the sheath, and the fixed sensor as the second sensor stays fixed relative to anatomy.

The inverse of the mechanism in FIG. 3 is also possible. Here, a fixed wire containing the fixed sensor as the second sensor (i.e., the reference sensor) is positioned within a movable outer sheath containing the movable sensor as the first sensor.

FIGS. 4A-4D together explain three-dimensional shape quantification of an implantable mitral valve during deployment.

Figure 4A:
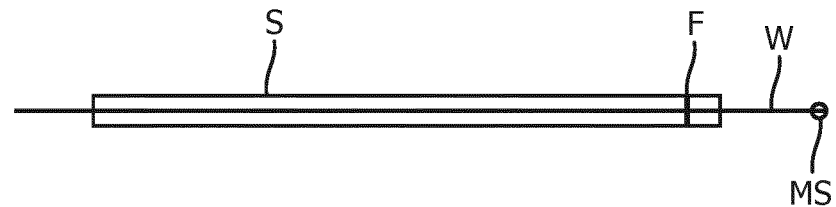
FIG. 4A illustrates another interventional medical device used for sensor-based shape identification, in accordance with a representative embodiment.

FIG. 4A illustrates an interventional medical device used for sensor-based shape identification, in accordance with a representative embodiment. Whereas the mechanism of FIG. 3 can be tightly integrated with the physical deployment of any device to allow the user to easily deploy a device and obtain the shape/path of the deployment in a single step without needing to perform a manual pullback, an example application of the device is shown in FIG. 4A, where the mechanism is integrated with an implantable mitral valve. The working channel of the mitral valve serves as the sheath S which is a sheath and/or conduit. The wire W is an implant guidewire that contains the movable sensor MS as the first sensor, and as the wire W is deployed within the valve, shape is tracked using three-dimensional ultrasound.

Similarly, deployment of the mechanism of FIG. 4A can be automated in a manner that allows discrimination between tissue movement and probe movement. When the pullback velocity is controlled, probe and tissue motion can be differentiated from the deployment more clearly. That is, tissue motions will result in deviations from the controlled and therefore expected velocities of the moving sensor MS to the fixed sensor at the fixed location F, or deviations from the expected changes in measured distance, whereas probe motions will not result in such deviations from expected measurements of such velocities or distances. A controller can measure movement of the imaging probe based on movement together of the first sensor and the second sensor, as well as based on movement of the first sensor relative to the second sensor. That is, a controller can measure when either sensor moves with or relative to the other, or when a sensor and a fixed location moves with or relative to the other.

In FIG. 4A, a mitral valve device includes a working channel as the sheath S and a guidewire as the wire W. The moving sensor MS is implanted on or in the guidewire as the wire W, and the fixed sensor at the fixed location F is on or in the working channel as the sheath S.

Figure 4B:
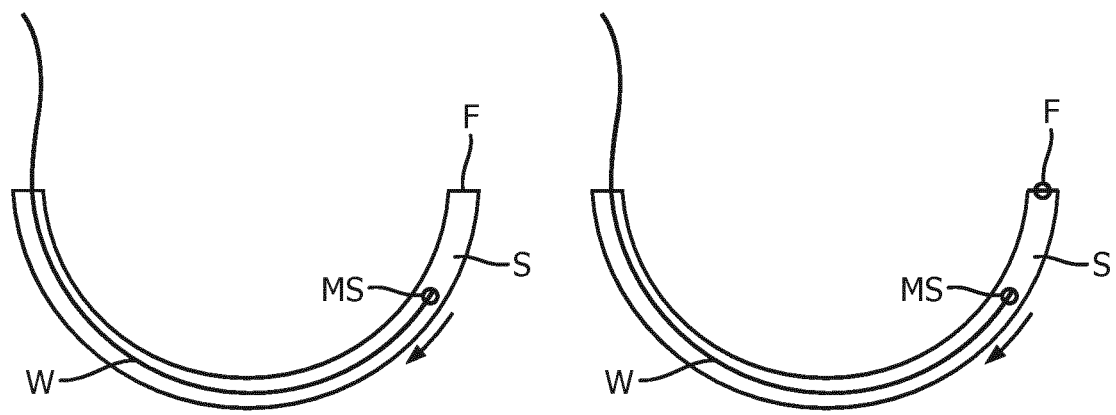
FIG. 4B illustrates operation of the interventional medical device used for sensor-based shape identification in FIG. 4A, in accordance with a representative embodiment.

FIG. 4B illustrates operation of the interventional medical device used for sensor-based shape identification in FIG. 4A, in accordance with a representative embodiment.

FIG. 4B shows that, as the mitral valve device is deployed, the guidewire as the wire W is moved along the inner working channel of the device as the sheath S. The distal end of the working channel as the sheath S contains the fixed reference sensor as the fixed sensor at the fixed location F, and shape is determined based on either forward or pullback movement of the wire W.

Figure 4C:
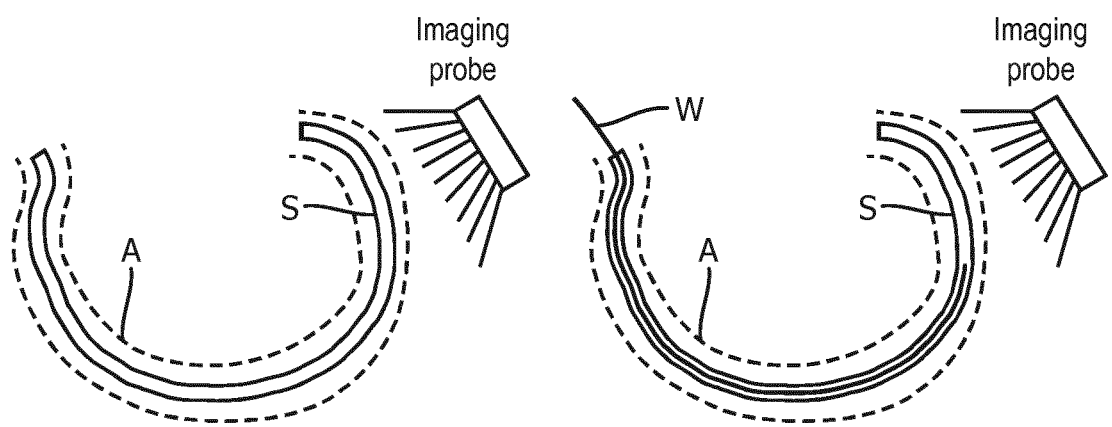
FIG. 4C illustrates the operation of the interventional medical device used for sensor-based shape identification in FIG. 4A, in accordance with a representative embodiment.

FIG. 4C illustrates an operation of the interventional medical device used for sensor-based shape identification in FIG. 4A, in accordance with a representative embodiment. In FIG. 4C, a target anatomy A, for example a mitral valve, is difficult to visualize directly in a three-dimensional (3D) ultrasound image. This illustrates why a distinctive visualization of the shape can be useful, such as when the shape of anatomy A is highlighted by color or lighting so as to offset the shape of anatomy A relative to the ultrasound image of tissue.

Figure 4D:
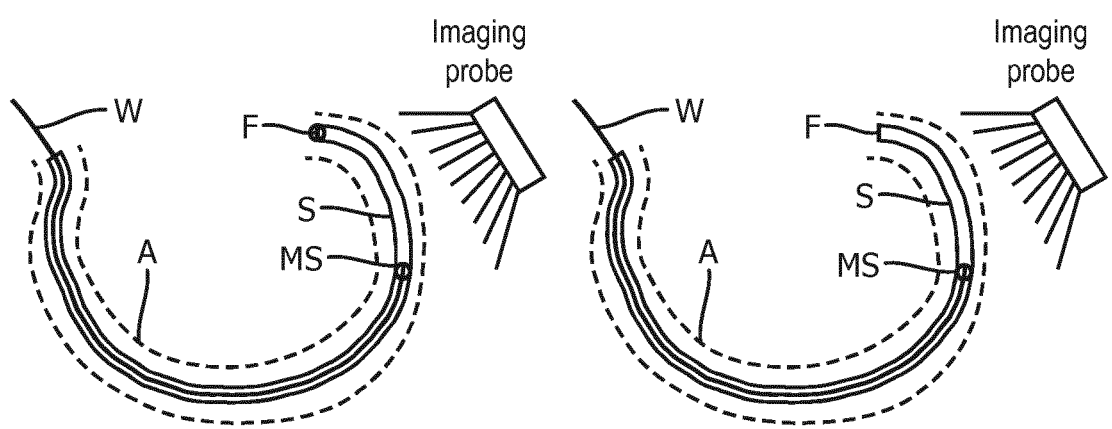
FIG. 4D illustrates another operation of the interventional medical device used for sensor-based shape identification in FIG. 4A, in accordance with a representative embodiment.

FIG. 4D illustrates another operation of the interventional medical device used for sensor-based shape identification in FIG. 4A, in accordance with a representative embodiment. In FIG. 4D, the three-dimensional (3D) ultrasound image with segmentation overlay based on shape from InSitu shows the interventional medical device and a target anatomy A, such as a mitral valve, much more clearly than in FIG. 4C.

Figure 5:
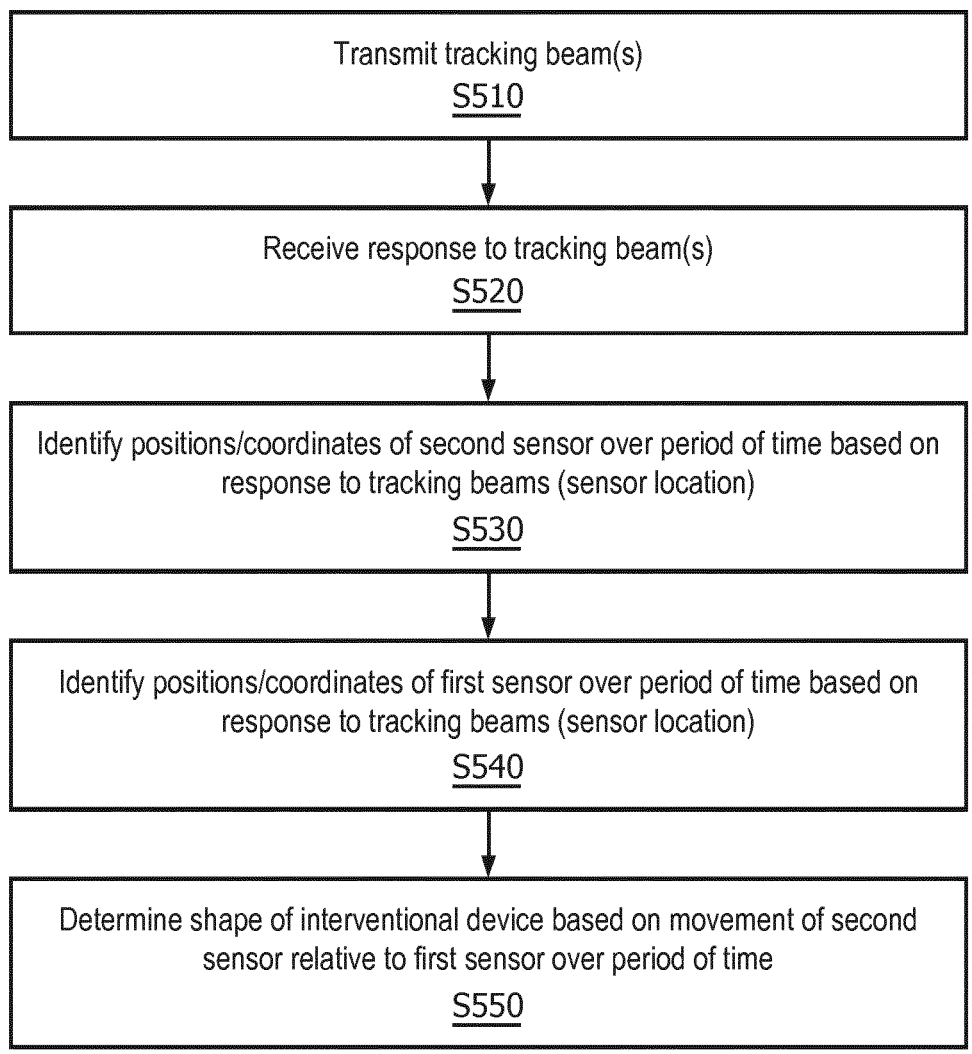
FIG. 5 illustrates a process for sensor-based shape identification, in accordance with a representative embodiment.

FIG. 5 illustrates a process for sensor-based shape identification, in accordance with a representative embodiment. In FIG. 5, the process starts at S510 by transmitting one or more tracking beams. At S520, the response to the tracking beams is received. At S530, positions and/or coordinates of a second sensor are identified over a period of time based on a response to tracking beams, to provide sensor location of the second sensor for each of multiple points in time. At S540, positions and/or coordinates of a first sensor are identified over a period of time based on a response to tracking beams, to provide sensor location of the first sensor for each of the multiple points in time. At S550, a shape of the interventional device is determined based on movement of the second sensor relative to the first sensor over the period of time.

Figure 6:
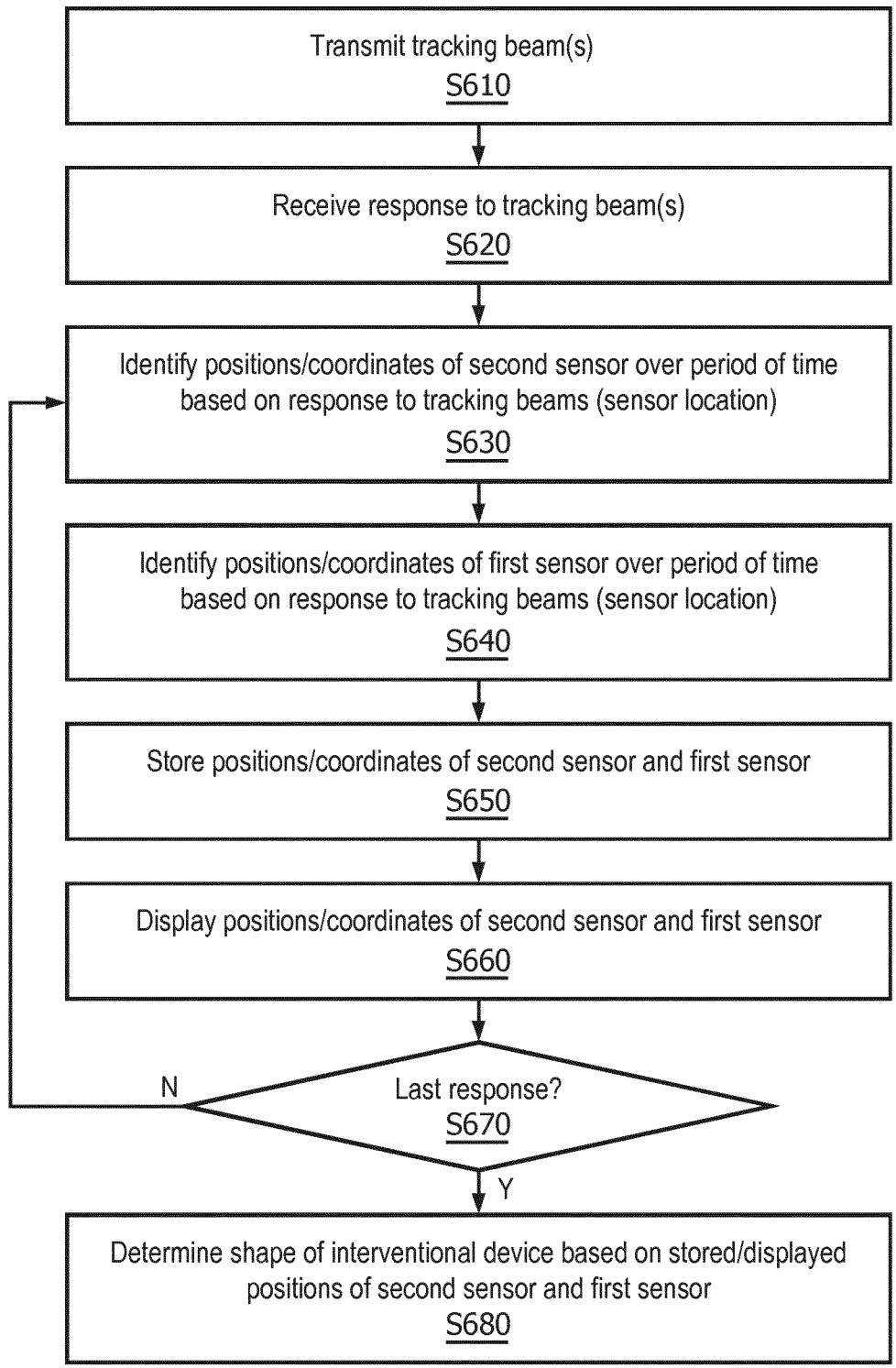
FIG. 6 illustrates another process for sensor-based shape identification, in accordance with a representative embodiment.

FIG. 6 illustrates another process for sensor-based shape identification, in accordance with a representative embodiment.

The process in FIG. 6 starts by transmitting tracking beams at S610. At S620, a response to the tracking beams is received. At S630, positions and/or coordinates of a second sensor are identified over a period of time based on a response to the tracking beams. At S640, positions and/or coordinates of a first sensor are identified over a period of time based on a response to the tracking beams. At S650, positions and/or coordinates of the second sensor and first sensor are stored. At S660, positions and/or coordinates of the second sensor and first sensor are displayed. At S670, a determination is made whether the response to the tracking beams is the last response. If the response to the tracking beams at S620 is not the last response (S670=No), the process returns to S630 to again identify positions and/or coordinates of a second sensor over a period of time based on a response to the tracking beams. If the response to the tracking beams at S620 is the last response (S670=Yes), at S680 the shape of the interventional device is determined based on stored/displayed positions of the second sensor and the first sensor.

Although not illustrated in FIG. 6, the determined shape of an interventional device can be automatically or visually compared with an expected shape of the interventional device to ensure the interventional device is progressing properly. For example, the process may include generating and projecting an expected shape of the interventional medical device before controlling the imaging probe, and then comparing the shape of the interventional medical device with the expected shape after determining the shape of the interventional medical device. Similarly, the process may include generating and projecting an expected path of the interventional medical device or an expected path of the moving sensor and then comparing the path of the interventional medical device or the path of the moving sensor to the expected path.

Figure 7:
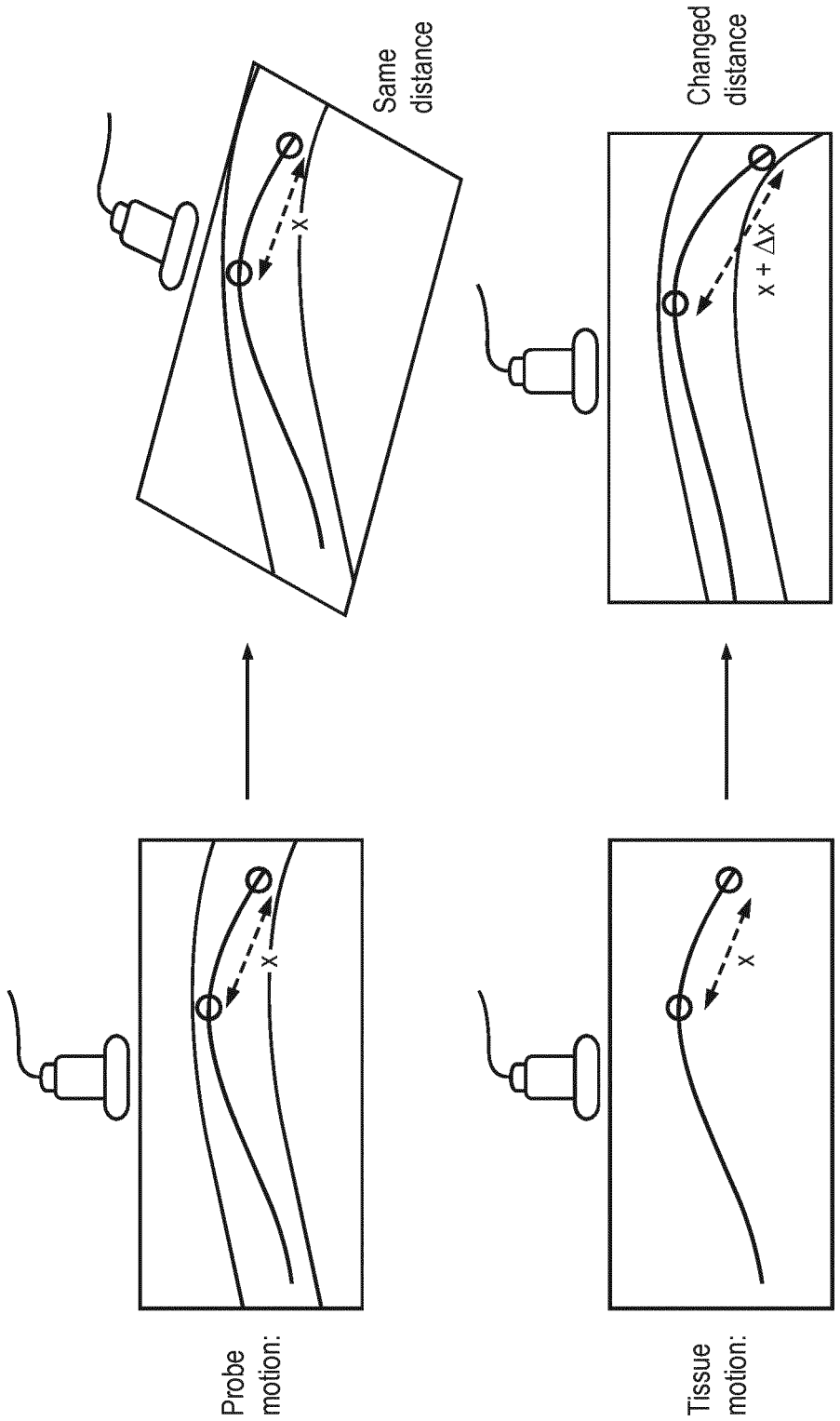
FIG. 7 illustrates a sequence in which fixed sensor can be used to isolate probe motion for sensor-based shape identification, in accordance with a representative embodiment.

FIG. 7 illustrates a sequence in which fixed sensor can be used to isolate probe motion for sensor-based shape identification, in accordance with a representative embodiment.

For situations in which both sensors are static, probe and tissue motion can again be differentiated, since probe motion will cause both sensors to move together whereas tissue motion likely will not (see FIG. 7). Specifically, when both sensors are static, tissue motions will result in variation of the measured moving-to-fixed sensor distance, whereas probe motions will not affect the sensor distance. A controller can measure movement of the imaging probe based on movement together of the first sensor and the second sensor, as well as based on movement of the first sensor relative to the second sensor.

For structural heart applications, the described mechanism can also be used to directly determine the cardiac cycle/cardiac motion. Here, as the position profiles of one or both the sensors are tracked over time, cyclical patterns in the temporal profile can be observed. The phase of the motion profiles indicates the cardiac cycles, and the magnitude of position change can be used to estimate cardiac motion. Notably, cardiac motion is not provided by ECG alone, but can be estimated from the magnitude of position change.

As noted above, when both sensors are static, tissue motions will result in variation of the measured moving-to-fixed sensor distance, whereas probe motion will not affect the sensor distance. Similarly, during automated pullback where the velocity is known, tissue motions will result in deviations of the measured moving-to-fixed velocity (or change in measured distance) from the known velocity (or changed in measured distance), whereas probe motions will not result in such deviations. The same principles apply when the pullback motion is coupled with device deployment.

As an example, sensor-based shape identification can be used for and with image-guided therapy (IGT) systems and devices. Sensor-based shape identification can be used to check that an interventional device has the correct shape and path during deployment, to detect an irregular path during an invasive procedure (e.g., septal puncture or chronic total occlusion crossing), to quantify a three-dimensional shape of implants (e.g., mitral valve implants) during tissue/organ repair (e.g., structural heart repair), and even to directly estimate cardiac cycle/cardiac motion using a static reference sensor.

Although sensor-based shape identification has been described with reference to several exemplary embodiments, it is understood that the words that have been used are words of description and illustration, rather than words of limitation. Changes may be made within the purview of the appended claims, as presently stated and as amended, without departing from the scope and spirit of sensor-based shape identification in its aspects. Although sensor-based shape identification has been described with reference to particular means, materials and embodiments, sensor-based shape identification is not intended to be limited to the particulars disclosed; rather sensor-based shape identification extends to all functionally equivalent structures, methods, and uses such as are within the scope of the appended claims.

For example, sensor-based shape identification can be used in structural heart repair, such as to check to ensure correct shape/path during device deployment, to detect whether the device has left a desired path during invasive procedures such as septal punctures, to quantify three-dimensional shape of mitral valve and other implants during structural heart repair, to directly estimate the cardiac cycle/cardiac motion using the static reference sensor, and/or to differentiate cardiac motion versus probe motion based on the relative position and velocity between sensors. An example of detecting whether the device has left a desired path during invasive procedures may involve, for example, a reference marker being placed at the location of the target anatomy.

In another example, sensor-based shape identification can be used for peripheral vascular intervention, such as to monitor wire shape during stenosis or occlusion crossings to detect wire buckling, and/or to detect wire progression with respect to the vessel to check if the wire has exited the vessel wall.

In other examples involving interventional procedures, sensor-based shape identification can be used to detect needle bending during deep tissue biopsy, and/or to provide a reliable in-body two-dimensional (2D) projection or three-dimensional (3D) projection fiducial registering the ultrasound to external imaging modalities, including but not limited to X-ray imaging, optical imaging, or computed tomography imaging.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A controller for determining shape of an interventional medical device, the controller comprising:
 a processor communicatively coupled to memory, the processor configured to:
  control an imaging probe to emit at least one tracking imaging beam to the interventional medical device over a period of time comprising a plurality of different points in time;
  receive, at each of the plurality of different points in time, a response to the at least one tracking imaging beam from a first sensor fixed on a first portion of the interventional medical device and a second sensor fixed at a fixed location on a second portion of the interventional medical device, wherein, during the period of time, the first portion, with the first sensor, moves along the interventional medical device relative to the second sensor at the fixed location;
  determine a plurality of positions of the first sensor corresponding to the plurality of different points in time based on the received response to the at least one tracking imaging beam from the first sensor;
  determine a path of movement of the first sensor relative to the second sensor based on the plurality of positions of the first sensor at the plurality of different points in time; and
  derive a shape of the interventional medical device based on the determined path of movement of the first sensor relative to the second sensor.

2. The controller of claim 1, wherein:
the first sensor moves relative to the second sensor by the first portion being moved relative to the second portion.

3. The controller of claim 2, wherein the first sensor is fixed in position on the first portion, and the first sensor moves relative to the second sensor by the first portion being moved relative to the second portion.

4. The controller of claim 1,
wherein the first portion with the first sensor is movable within the second portion.

5. The controller of claim 1,
wherein the second portion with the second sensor is moveable within the first portion.

6. The controller of claim 1, wherein the first portion comprises a wire and the second portion comprises a conduit or sheath.

7. The controller of claim 1, wherein the processor is further configured to:
   detect a change in position of the second sensor indicating at least one of tissue motion and imaging probe motion,
   provide adjustment to one or more of the determined plurality of positions of the first sensor based on the changed position of the second sensor to compensate for the at least one of tissue motion and imaging probe motion, and
   determine the path of movement to account for the adjustment to the one or more of the determined plurality of positions of the first sensor.

8. A method for determining shape of an interventional medical device, comprising:
   controlling an imaging probe to emit at least one tracking imaging beam to an interventional medical device over a period of time comprising a plurality of different points in time;
   receiving, at each of the plurality of different points in time, a response to the at least one tracking imaging beam from a first sensor fixed on a first portion of the interventional medical device and a second sensor fixed at a fixed location on a second portion of the interventional medical device, wherein-during the period of time, the first portion, with the first sensor, moves along the interventional medical device relative to the second sensor at the fixed location;
   determining a plurality of positions of the first sensor corresponding to the plurality of different points in time based on the received response to the at least one tracking imaging beam from the first sensor;
   determining a path of movement of the first sensor relative to the second sensor based on the plurality of positions of the first sensor at the plurality of different points in time; and
   deriving a shape of the interventional medical device based on the determined path of movement of the first sensor relative to the second sensor.

9. The method of claim 8, wherein:
   the first sensor moves relative to the second sensor by the first portion being moved relative to the second portion.

10. The method of claim 9, wherein the first sensor is fixed in position on the first portion, and the first sensor moves relative to the second sensor by the first portion being moved relative to the second portion.

11. The method of claim 8,
   wherein the first portion with the first sensor is movable within the second portion.

12. The method of claim 8,
   wherein the second portion with the second sensor is movable within the first portion.

13. The method of claim 8, further comprising:
   projecting an expected shape of the interventional medical device before controlling the imaging probe; and
   comparing the shape of the interventional medical device with the expected shape after determining the shape of the interventional medical device.

14. The method of claim 8, further comprising:
   receiving the response to the at least one tracking imaging beam from the first sensor and the second sensor fixed at the fixed location.

15. The method of claim 8, further comprising:
   detecting a change in position of the second sensor indicating at least one of tissue motion and imaging probe motion,
   providing adjustment to one or more of the determined plurality of positions of the first sensor based on the changed position of the second sensor to compensate for the at least one of tissue motion and imaging probe motion, and
   determining the path of movement to account for the adjustment to the one or more of the determined plurality of positions of the first sensor.

16. A non-transitory computer-readable storage medium comprising instructions which, when executed by a processor, cause the processor to:
   control an imaging probe to emit at least one tracking imaging beam to an interventional medical device over a period of time comprising a plurality of different points in time;
   receive, at each of the plurality of different points in time, a response to the at least one tracking imaging beam from a first sensor fixed on a first portion of the interventional medical device and a second sensor fixed at a fixed location on a second portion of the interventional medical device, wherein during the period of time, the first portion, with the first sensor, moves along the interventional medical device relative to the second sensor at the fixed location;
   determine a plurality of positions of the first sensor corresponding to the plurality of different points in time based on the received response to the at least one tracking imaging beam from the first sensor;
   determine a path of movement of the first sensor relative to the second sensor based on the plurality of positions of the first sensor at the plurality of different points in time; and
   derive a shape of the interventional medical device based on the determined path of movement of the first sensor relative to the second sensor.

17. The non-transitory computer-readable storage medium of claim 16, wherein the instructions, when executed by the processor, further cause the processor to:
   detect a change in position of the second sensor indicating at least one of tissue motion and imaging probe motion,
   provide adjustment to one or more of the determined plurality of positions of the first sensor based on the changed position of the second sensor to compensate for the at least one of tissue motion and imaging probe motion, and
   determine the path of movement to account for the adjustment to the one or more of the determined plurality of positions of the first sensor.

* * * * *